United States Patent [19]

Shayesteh et al.

[11] Patent Number: 6,110,673
[45] Date of Patent: Aug. 29, 2000

[54] GENETIC ALTERATIONS ASSOCIATED WITH CANCER

[75] Inventors: Laleh Shayesteh, Foster City; Joe W. Gray, San Francisco, both of Calif.

[73] Assignee: The Regents of the University of California, Oakland, Calif.

[21] Appl. No.: 08/837,046

[22] Filed: Apr. 5, 1997

Related U.S. Application Data

[63] Continuation of application No. 08/783,729, Jan. 16, 1997.

[51] Int. Cl.[7] .................................................. C12Q 1/68
[52] U.S. Cl. ............................................................ 435/6
[58] Field of Search .................................. 435/6; 536/23.5

[56] References Cited

PUBLICATIONS

Thompson et al. Cancer Genet Cytogenet. 87: 55–62 (1996).

*Primary Examiner*—Lisa B. Arthur
*Attorney, Agent, or Firm*—Townsend and Townsend and Crew LLP

[57] ABSTRACT

The present invention provides new probes for the detection of chromosomal alterations associated with cancer, particularly ovarian cancer. The probes bind selectively with target nucleic acid sequences at 3q26 and at 19q13.1–19q13.2.

2 Claims, 6 Drawing Sheets

GENETIC ALTERATIONS ASSOCIATED WITH CANCER

CROSS REFERENCE TO RELATED APPLICATIONS

This is a continuation in part of copending application, U.S. Ser. No. 08/783,729, filed Jan. 16, 1997, now allowed which is incorporated herein by reference.

STATEMENT REGARDING FEDERALLY SPONSORED RESEARCH

This invention was made with Government support under Grant No. CA09215 awarded by the National Institutes of Health. The Government has certain rights in this invention.

BACKGROUND OF THE INVENTION

Molecular genetic mechanisms responsible for the development and progression of many cancers remain largely unknown. Identification of sites of frequent and recurring allelic deletion or gain is a first step toward identifying some of the important genes involved in the malignant process. Previous studies in retinoblastoma (Friend, et al. Nature, 323:643–6 (1986)) and other cancers (Cawthon, et al., Cell, 62:193–201 (1990); Baker, et al., Science, 244:217–21 (1989); Shuin, et al., Cancer Res, 54:2832–5 (1994)) have amply demonstrated that definition of regional chromosomal deletions occurring in the genomes of human tumors can serve as useful diagnostic markers for disease and are an important initial step towards identification of critical genes. Similarly, regions of common chromosomal gain have been associated with amplification of specific genes (Visakorpi, et al., Nature Genetics, 9:401–6 (1995)).

Comparative genomic hybridization (CGH) is a relatively new molecular technique used to screen DNA from tumors for regional chromosomal alterations (Kallioniemi, et al., Science, 258:818–21 (1992) and WO 93/18186). Unlike microsatellite or Southern analysis allelotyping studies, which typically sample far less than 0.1% of the total genome, a significant advantage of CGH is that all chromosome arms are scanned for losses and gains. Moreover, because CGH does not rely on naturally occurring polymorphisms, all regions are informative, whereas polymorphism-based techniques are limited by homozygous (uninformative) alleles among a fraction of tumors studied at every locus.

Increases in copy number in the long arm of chromosome 3, in particular 3q25-3qter, has been associated with cancer. Increases in copy number in this area have been seen not only in ovarian tumors (Iwabuchi et al., Cancer Research 55:6172–8180 (1995) but also in brain tumors, head and neck cancer, lung cancer, ductal breast cancer, renal cell and other urinary tract cancers, and cervical cancer. Ried et al., Genes Chromosomes Cancer 15:234–45 (1996); Yeatman et al. Clin Exp Metastasis 14:246–52 (1996); Brzoska et al., Cancer Res 15:3055–9 (1995); Ried et al., Cancer Res 54:1801–6 (1994); and Speicher et al., Cancer Res 55:1010–3 (1995).

The identification of narrower regions of genetic alteration or genes associated with cancers such as ovarian cancer would be extremely useful in the early diagnosis or prognosis of these diseases. The present invention addresses these and other needs.

SUMMARY OF THE INVENTION

The present invention provides compositions and methods for detecting genetic alterations correlated with cancer. The invention can be used to detect alterations in a 2 MB region at 3q26.3 that are associated with a number of cancers. Examples include ovarian cancer, brain cancer, lung cancer, head and neck tumors, renal cell and other urinary tumors, cervical cancer, and ductal breast cancer. The invention is particularly useful for detecting alterations associated with ovarian cancer.

The methods comprise contacting a nucleic acid sample from a patient with a probe which binds selectively to a target nucleic acid sequence on 3q26.3 correlated with cancer. In particular, the invention provides sequences from genes encoding the catalytic subunit of phosphatidylinositol kinase type 3 (PIK3CA) or the glucose transporter, GLUT2. The probes of the invention are contacted with the sample under conditions in which the probe binds selectively with the target nucleic acid sequence to form a hybridization complex. The formation of the hybridization complex is then detected. Typically, the number of regions of hybridization are counted. Abnormalities are detected as increases above normal in the regions of hybridization. In some embodiments, the methods of the invention further comprise detection of amplifications at 19q13.1–13.2. This region includes AKT2, a putative oncogene.

Alternatively, sample DNA from the patient can be fluorescently labeled and competitively hybridized against fluorescently labeled normal DNA to normal lymphocyte metaphases or to arrays of nucleic acid molecules which map to 3q26.3. Alterations in DNA copy number in the sample DNA are then detected as increases in sample DNA as compared to normal DNA at the 3q26.3 region.

Definitions

A "nucleic acid sample" as used herein refers to a sample comprising DNA in a form suitable for hybridization to a probes of the invention. The nucleic acid may be total genomic DNA, total mRNA, genomic DNA or mRNA from particular chromosomes, or selected sequences (e.g. particular promoters, genes, amplification or restriction fragments, cDNA, etc.) within particular cancer-associated amplifications. The nucleic acid sample may be extracted from particular cells or tissues. The tissue sample from which the nucleic acid sample is prepared is typically taken from a patient suspected of having the disease associated with the amplification being detected. The sample may be prepared such that individual nucleic acids remain substantially intact and typically comprises interphase nuclei prepared according to standard techniques. A "nucleic acid sample" as used herein may also refer to a substantially intact condensed chromosome (e.g. a metaphase chromosome). Such a condensed chromosome is suitable for use as a hybridization target in in situ hybridization techniques (e.g. FISH). The particular usage of the term "nucleic acid sample" (whether as extracted nucleic acid or intact metaphase chromosome) will be readily apparent to one of skill in the art from the context in which the term is used. For instance, the nucleic acid sample can be a tissue or cell sample prepared for standard in situ hybridization methods described below. The sample is prepared such that individual chromosomes remain substantially intact and typically comprises metaphase spreads or interphase nuclei prepared according to standard techniques.

The sample may also be isolated nucleic acids immobilized on a solid surface (e.g., nitrocellulose) for use in Southern or dot blot hybridizations and the like. In some embodiments, the probe may be a member of an array of nucleic acids as described, for instance, in WO 96/17958. In some cases, the nucleic acids may be amplified using standard techniques such as PCR, prior to the hybridization. The sample is typically taken from a patient suspected of having cancer associated with the abnormality being detected.

"Nucleic acid" refers to a deoxyribonucleotide or ribonucleotide polymer in either single- or double-stranded form, and unless otherwise limited, would encompass known analogs of natural nucleotides that can function in a similar manner as naturally occurring nucleotides.

"Subsequence" refers to a sequence of nucleic acids that comprise a part of a longer sequence of nucleic acids.

A "probe" or a "nucleic acid probe", as used herein, is defined to be a collection of one or more nucleic acid fragments whose hybridization to a target can be detected. The probe is typically labeled as described below so that its binding to the target can be detected. In some embodiments, the sample comprising the target nucleic acid is labeled and the probe is not labeled. For instance, when the probes are prepared as an array of nucleic acids which selectively bind a number of desired target sequences.

The probe is produced from a source of nucleic acids from one or more particular (preselected) portions of the genome, for example one or more clones, an isolated whole chromosome or chromosome fragment, or a collection of polymerase chain reaction (PCR) amplification products. The probes of the present invention are produced from nucleic acids found in the regions of genetic alteration as described herein. The probe may be processed in some manner, for example, by blocking or removal of repetitive nucleic acids or enrichment with unique nucleic acids. Thus the word "probe" may be used herein to refer not only to the detectable nucleic acids, but to the detectable nucleic acids in the form in which they are applied to the target, for example, with the blocking nucleic acids, etc. The blocking nucleic acid may also be referred to separately. What "probe" refers to specifically is clear from the context in which the word is used.

"Hybridizing" refers the binding of two single stranded nucleic acids via complementary base pairing.

"Bind(s) substantially" or "binds specifically" or "binds selectively" or "hybridizing specifically to" refers to complementary hybridization between a probe and a target sequence and embraces minor mismatches that can be accommodated by reducing the stringency of the hybridization media to achieve the desired detection of the target nucleic acid sequence. These terms also refer to the binding, duplexing, or hybridizing of a molecule only to a particular nucleotide sequence under stringent conditions when that sequence is present in a complex mixture (e.g., total cellular) DNA or RNA. The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. Typically, stringent conditions will be those in which the salt concentration is at least about 0.02 Na ion concentration (or other salts) at pH 7.0 to 8.3 and the temperature is at least about 60° C. Stringent conditions may also be achieved with the addition of destabilizing agents such as formamide.

One of skill will recognize that the precise sequence of the particular probes described herein can be modified to a certain degree to produce probes that are "substantially identical" to the disclosed probes, but retain the ability to bind substantially to the target sequences. Such modifications are specifically covered by reference to the individual probes herein. The term "substantial identity" of nucleic acid sequences means that a nucleic acid comprises a sequence that has at least 90% sequence identity, more preferably at least 95%, compared to a reference sequence using the methods described below using standard parameters.

Two nucleic acid sequences are said to be "identical" if the sequence of nucleotides in the two sequences is the same when aligned for maximum correspondence as described below. The term "complementary to" is used herein to mean that the complementary sequence is identical to all or a portion of a reference nucleic acid sequence.

Sequence comparisons between two (or more) nucleic acids are typically performed by comparing sequences of the two sequences over a "comparison window" to identify and compare local regions of sequence similarity. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2: 482 (1981), by the homology alignment algorithm of Needleman and Wunsch *J. Mol. Biol.* 48:443 (1970), by the search for similarity method of Pearson and Lipman *Proc. Natl. Acad. Sci.* (*U.S.A.*) 85: 2444 (1988), by computerized implementations of these algorithms.

"Percentage of sequence identity" is determined by comparing two optimally aligned sequences over a comparison window, wherein the portion of the nucleic acid sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Another indication that nucleotide sequences are substantially identical is if two molecules hybridize to the same sequence under stringent conditions. Stringent conditions are sequence dependent and will be different in different circumstances. Generally, stringent conditions are selected to be about 5° C. lower than the thermal melting point ($T_m$) for the specific sequence at a defined ionic strength and pH. The Tm is the temperature (under defined ionic strength and pH) at which 50% of the target sequence hybridizes to a perfectly matched probe. Typically, stringent conditions will be those as described above.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The phrase "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to a protein under such conditions may require an antibody that is selected for its specificity for a particular protein. For example, antibodies can be raised to the particular proteins disclosed here. Such antibodies will bind the proteins and not any other proteins present in a biological sample. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

DESCRIPTION OF THE PREFERRED EMBODIMENT

Figure 1:
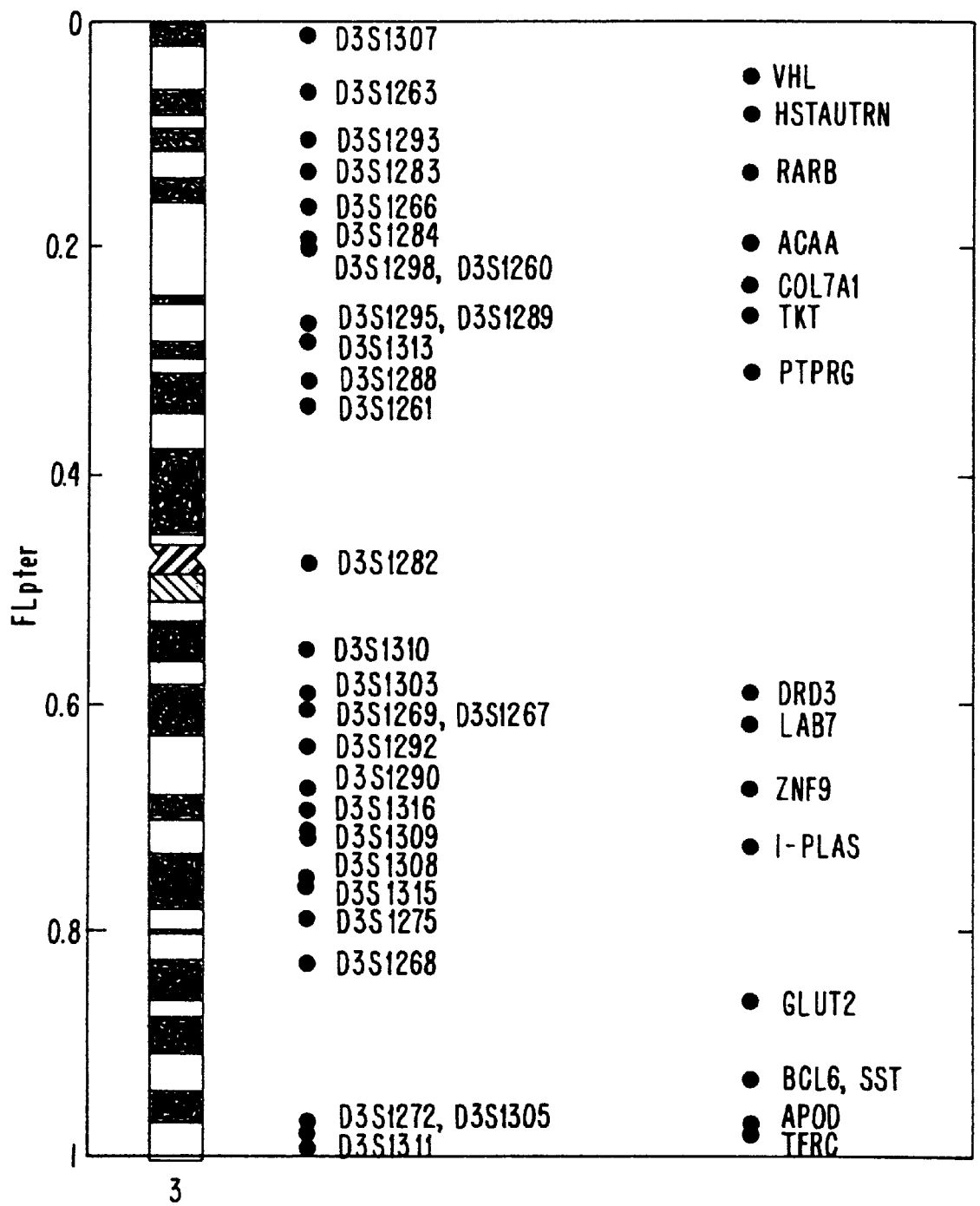
FIG. 1 shows a physical map of P1 probes along chromosome 3. The P1 clonness were picked using STSs of known genetic location along chromosome 3. P1 clones corresponding to genes were picked using PCR primers specific to each gene.

Identification of Chromosomal Regions and Genes Associated With Cancer

The present invention is based on a comprehensive molecular cytogenetic analysis of the genomes of ovarian cancer cells using comparative genomic hybridization (CGH). CGH studies on epithelial ovarian cancer have revealed several regions that are present in increased or decreased copy number. More than 40% of these tumors show an increase in copy number on the long arm of chromosome 3, in particular in the region of 3q25–3qter (Iwabuchi et al., supra). This increase in copy number seems to be an early event for ovarian cancer. Increases in copy number in this region have also been observed in brain tumors, lung cancer, head and neck tumors, renal cell and other urinary tumors, cervical cancer, and ductal breast cancer.

Genomic regions that are found to be sites of increased DNA copy number in a large fraction of the cell lines and primary tumor cells are likely to include oncogenes that are present at increased copy number and hence overexpressed. Gene amplification is one method by which cells escape from normal controls of proliferation. The resulting overexpression or altered expression of these genes and their products is believed to play an important role in the development of a variety of human cancers (Weinberg, *Cancer* 61:1963–1968 (1988); Bishop, *Cell* 64: 235–248 (1991)).

The present invention is based in part on the discovery of specific cloned genomic DNA sequences showing increased copy number in a 2 MB region at 3q26.3 region. Increased copy number was assessed using FISH and a number of P1, YAC, and cosmid clones known to map to this region. As shown below, one of the P1 clones and 5 YAC clones associated with the region have shown an increase in copy number in 5 out of 5 ovarian cancer cell line and 6 out of 6 tumor samples tested. The P1 was picked using PCR primers specific to the Glucose transporter gene, GLUT2. This gene is responsible for glucose signaling for beta cell insulin release. Its RNA product is found mostly in adult liver and pancreas, specifically in insulin-producing beta cells (Fukumoto et al., *Proc. Nat. Acad. Sci.* 85:5434–5438 (1988)). The sequence of cDNA from the gene is described in Fukumoto et al. This gene has been associated with is non-insulin-dependent diabetes mellitus (NIDDM). In NIDDM the highly conserved regions of this gene have been found mutated, resulting in abolished transport activity of the gene (Mueckler et al., *J. Biol. Chem.* 269:17765–17767 (1994)).

The 3q26 region also harbors the sequences for another gene, the catalytic subunit of phosphatidylinositol kinase type 3 (PI3K). The cloning of cDNA and genomic DNA encoding the catalytic subunit is described in Volinia et al. *Genomics* 24:472–477 (1994) and WO93/21328.

PI3K is a heterodimeric enzyme comprising a 110-kDa catalytic subunit (PIK3CA) and an 85 kD regulatory subunit that binds to tyrosine phosphopeptide sites linked to receptors serving diverse signal functions. Along with its regulatory subunit, PIK3CA binds to growth factor receptors or associated signal complex proteins after ligand induced activation, and phosphorylates phosphoinositides. The lipid products generated by PI3K accumulate in cells activated by growth factors (Parker and Waterfield, *Cell Growth and Differentiation* 3:747–752 (1992)) or in cells transformed by the polyoma middle T antigen (Serunian et al., *J. Virol.* 64:4718–4725 (1990)). PI3K is also associated with activated src (Fukui and Hanafusa, *Mol. Cell. Biol.* 9:1651–1658 (1989)). Relatively little is known about the mechanism of signal transduction for PI3K. A proto-oncogene product, the serine/threonine kinase known as protein kinase B (PKB, also known as AKT and Rac), has been placed downstream of PI3K (see, Burgering and Coffer, *Nature* 376:599–602 (1995); Franke et al., *Cell* 81:727–736 (1995)). The AKT2 oncogene has itself shown amplification at the DNA and RNA level in ovarian cancer samples (Bellacosa et al., *Int. J. Cancer* 64:280–285 (1995)).

In addition, PI3K activity is required to maintain basal and insulin-stimulated glucose and amino acid transport (Tsakiridis et al., *Endocrinology* 136:4315–4322 (1995)). It is therefore likely that an increased expression in PI3K levels could also upregulate the nearby GLUT2 gene. Compounds that inhibit expression of GLUT2 or inhibit activity of the protein have therapeutic potential in cancers, such as ovarian cancer. A number of glucose transport inhibitors are available. Exemplary glucose transport inhibitors include cytochalasin B and ethanol (see, e.g., Colville et al. *Biochemical Journal* 290:701–706 (1993) and Nagamatsu et al., *Bioch. Molec. Biol. Int.* 37:675–680 (1995)).

A number of high molecular weight kinases have been cloned that have sequence similarities to PIK3CA. These kinases have a range of cellular functions such as meiotic and V(D)j recombination, chromosome maintenance and repair, cell cycle progression, and cell cycle checkpoints, and with dysfunctions resulting in medical disorders ranging from a loss of immunological function to cancer. Therefore, increases in copy number in the PIK3CA in ovarian tumor samples may have implications in the level of tumor aggressiveness or patient prognosis, and the analysis of this gene at the tumor level could improve early diagnosis, and assist in better patient therapy and survival for this disease.

In some embodiments of the invention, probes specific to 19q13.1–13.2 can be used in the methods, as well. Amplification of this region has been correlated with ovarian cancer using FISH and molecular studies (see, e.g., Thompson et al. *Cancer Genet Cytogenet* 87: 55–62 (1996)). The AKT2 gene, discussed above, is located in this region. AKT2 encodes a member of a subfamily of protein-serine/threonine kinases and is thought to be a human homologue of an oncogene isolated from the retrovirus, AKT8. Staal, *Proc Natl Acad Sci U S A* 84:5034–7 (1987). A cDNA encoding the protein is described by Cheng et al. *Proc Natl Acad Sci USA* 89: 9267–71 (1992). Amplification of 19q13.1–13.2 region and overexpression of the AKT2 gene have been identified in ovarian and pancreatic cancer (see, e.g., Bellacosa et al., supra, Thompson et al. supra, and Miwa et al. *Biochem Biophys Res Commun* 225:968–74 (1996)). Inhibition of AKT2 expression and tumorigenicity has been demonstrated using antisense RNA. Cheng et al. *Proc Natl Acad Sci U S A* 93:3636–41 (1996).

AKT activity appears to be regulated by binding of phosphatidylinositol-3,4-biphosphate (Ptdins-3,4-$P_2$) to a pleckstrin homology domain. The activation of AKT has been associated with increased cell survival through a reduction in apoptosis. Without wishing to be bound by theory, it is believed that amplification of PIK3CA in ovarian cancer contributes to cancer progression and/or initiation by reducing apoptotic death and increasing cell proliferation rate. The possible decrease in apoptosis is relevant since apoptosis likely plays an important role removal of epithelial cells that become detached from the stroma during ovulation. Reduced apoptosis in these cells might lead to malignancy since severed studies now suggest that disruption of the stroma (e.g. by overexpression of metalloproteinases) causes cancer in murine mammary cells.

In the present invention it has been found that both the PIK3CA and AKT2 genes are amplified and overexpressed in cancers, such as ovarian cancer. Thus, detection of amplification and/or overexpression of both genes is useful in the early diagnosis of cancers.

In addition, in some embodiments, the expression of other genes associated with cancer (e.g., tumor suppressor genes or oncogenes) can be monitored in the present invention. For instance, expression of wild-type p53 can be monitored according to known techniques. Mutation or loss of the p53 gene is the most common genetic alteration in human cancers (Bartek et al. (1991) *Oncogene,* 6: 1699–1703, Hollstein et al. (1991) *Science,* 253: 49–53).

Preparation of Probes of the Invention

A number of methods can be used to identify probes which hybridize specifically to the 3q26 region other than those exemplified here. For instance, probes can be generated by the random selection of clones from a chromosome specific library, and then mapped to each chromosome or region by digital imaging microscopy. This procedure is described in U.S. Pat. No. 5,472,842. Briefly, a genomic or chromosome specific DNA is digested with restriction enzymes or mechanically sheared to give DNA sequences of at least about 20 kb and more preferably about 40 kb to 300 kb. Techniques of partial sequence digestion are well known in the art. See, for example Perbal, *A Practical Guide to Molecular Cloning* 2nd Ed., Wiley N.Y. (1988). The resulting sequences are ligated with a vector and introduced into the appropriate host. Exemplary vectors suitable for this purpose include cosmids, yeast artificial chromosomes (YACs), bacterial artificial chromosomes (BACs) and P1 phage. Typically, cosmid libraries are prepared. Various libraries spanning entire chromosomes are also available commercially from for instance Genome Systems.

Once a probe library is constructed, a subset of the probes is physically mapped on the selected chromosome. FISH and digital image analysis can be used to localize clones along the desired chromosome. Briefly, the clones are mapped by FISH to metaphase spreads from normal cells using e.g., FITC as the fluorophore. The chromosomes may be counterstained by a stain which stains DNA irrespective of base composition (e.g., propidium iodide), to define the outlining of the chromosome. The stained metaphases are imaged in a fluorescence microscope with a polychromatic beam-splitter to avoid color-dependent image shifts. The different color images are acquired with a CCD camera and the digitized images are stored in a computer. A computer program is then used to calculate the chromosome axis, project the two (for single copy sequences) FITC signals perpendicularly onto this axis, and calculate the average fractional length from a defined position, typically the p-telomere. This approach is described, for instance, in U.S. Pat. No. 5,472,842.

Sequence information of the genes identified here permits the design of highly specific hybridization probes or amplification primers suitable for detection of target sequences from these genes. As noted above, the complete sequence of these genes is known. Means for detecting specific DNA sequences within genes are well known to those of skill in the art. For instance, oligonucleotide probes chosen to be complementary to a selected subsequence within the gene can be used. Alternatively, sequences or subsequences may be amplified by a variety of DNA amplification techniques (for example via polymerase chain reaction, ligase chain reaction, transcription amplification, etc.) prior to detection using a probe. Amplification of DNA increases sensitivity of the assay by providing more copies of possible target subsequences. In addition, by using labeled primers in the amplification process, the DNA sequences may be labeled as they are amplified.

Labeling Probes

Methods of labeling nucleic acids are well known to those of skill in the art. Preferred labels are those that are suitable for use in in situ hybridization. The nucleic acid probes may be detectably labeled prior to the hybridization reaction. Alternatively, a detectable label which binds to the hybridization product may be used. Such detectable labels include any material having a detectable physical or chemical property and have been well-developed in the field of immunoassays.

As used herein, a "label" is any composition detectable by spectroscopic, photochemical, biochemical, immunochemical, or chemical means. Useful labels in the present invention include radioactive labels (e.g. $^{32}P$, $^{125}I$, $^{14}C$, $^{3}H$, and $^{35}S$), fluorescent dyes (e.g. fluorescein, rhodamine, Texas Red, etc.), electron-dense reagents (e.g. gold), enzymes (as commonly used in an ELISA), colorimetric labels (e.g. colloidal gold), magnetic labels (e.g. Dynabeads™), and the like. Examples of labels which are not directly detected but are detected through the use of directly detectable label include biotin and dioxigenin as well as haptens and proteins for which labeled antisera or monoclonal antibodies are available.

The particular label used is not critical to the present invention, so long as it does not interfere with the in situ hybridization of the stain. However, stains directly labeled with fluorescent labels (e.g. fluorescein-12-dUTP, Texas Red-5-dUTP, etc.) are preferred for chromosome hybridization.

A direct labeled probe, as used herein, is a probe to which a detectable label is attached. Because the direct label is already attached to the probe, no subsequent steps are required to associate the probe with the detectable label. In contrast, an indirect labeled probe is one which bears a moiety to which a detectable label is subsequently bound, typically after the probe is hybridized with the target nucleic acid.

In addition the label must be detectible in as low copy number as possible thereby maximizing the sensitivity of the assay and yet be detectable above any background signal. Finally, a label must be chosen that provides a highly localized signal thereby providing a high degree of spatial resolution when physically mapping the stain against the chromosome. Particularly preferred fluorescent labels include fluorescein-12-dUTP and Texas Red-5-dUTP.

The labels may be coupled to the probes in a variety of means known to those of skill in the art. In some embodiments the nucleic acid probes are labeled using nick translation or random primer extension (Rigby, et al. *J. Mol. Biol.*, 113: 237 (1977) or Sambrook et al., *Molecular Cloning—A Laboratory Manual,* Cold Spring Harbor Laboratory, Cold Spring Harbor, N.Y., (1989)). Particularly preferred methods for labeling probes are described in U.S. Pat. No. 5,491,224. These methods involve direct labeling the probes by chemical modification of cytosine residues.

Use of Nucleic Acids of the Invention to Detect Chromosomal Alterations

Using the results provided here, one of skill can prepare nucleic acid probes specific to the 3q26 region of genetic alteration that is associated with ovarian and other cancer. In particular, nucleic acid sequences from the GLUT2 gene or the PIK3CA gene can be used to detect copy number increase of these genes. The probes can be used in a variety of nucleic acid hybridization assays to detect the presence (in particular increased copy number) of the target gene. Thus, the probes are useful, for example, in the early diagnosis or prognosis of cancer. As noted above, the probes are particularly useful for detecting alteration associated with ovarian cancer. The regions can also be used for a large number of other cancers as described above.

The genetic alterations are detected through the hybridization of a probe of this invention to a nucleic acid sample in which it is desired to screen for the alteration. Suitable hybridization formats are well known to those of skill in the art and include, but are not limited to, variations of Southern Blots, northern blots, CGH, in situ hybridization and quantitative amplification methods such as quantitative PCR (see, e.g. Sambrook et al., Kallioniemi et al., *Proc. Natl Acad Sci USA,* 89: 5321–5325 (1992), and *PCR Protocols, A Guide to Methods and Applications,* Innis et al., Academic Press, Inc. N.Y., (1990)).

The sample used in the methods will, of course, depend upon the particular method used to detect the target. For instance, the nucleic acid sample can be a tissue or cell sample prepared for standard in situ hybridization methods. The sample or probes may also be isolated nucleic acids immobilized on a solid surface (e.g., nitrocellulose) for use in Southern or dot blot hybridizations and the like. In some embodiments, the probes of the invention may comprise an array of nucleic acids as described, for instance, in WO96/17958).

In a preferred embodiment, the regions disclosed here are identified using in situ hybridization. Generally, in situ hybridization comprises the following major steps: (1) fixation of tissue or biological structure to analyzed; (2) prehybridization treatment of the biological structure to increase accessibility of target DNA, and to reduce nonspecific binding; (3) hybridization of the mixture of nucleic acids to the nucleic acid in the biological structure or tissue; (4) posthybridization washes to remove nucleic acid fragments not bound in the hybridization and (5) detection of the hybridized nucleic acid fragments. The reagent used in each of these steps and their conditions for use vary depending on the particular application.

In some applications it is necessary to block the hybridization capacity of repetitive sequences. In this case, human genomic DNA or Cot1 DNA is used as an agent to block such hybridization. The preferred size range is from about 200 bp to about 1000 bases, more preferably between about 400 to about 800 bp for double stranded, nick translated nucleic acids.

Hybridization protocols for the particular applications disclosed here are described in Pinkel et al. *Proc. Natl. Acad. Sci. USA*, 85: 9138–9142 (1988) and in EPO Pub. No. 430,402. Suitable hybridization protocols can also be found in *Methods in Molecular Biology Vol. 33: In Situ Hybridization Protocols*, K. H. A. Choo, ed., Humana Press, Totowa, N.J., (1994). In a particularly preferred embodiment, the hybridization protocol of Kallioniemi et al., *Proc. Natl Acad Sci USA*, 89: 5321–5325 (1992) is used.

Typically, it is desirable to use dual color FISH, in which two probes are utilized, each labeled by a different fluorescent dye. A test probe that hybridizes to the region of interest is labeled with one dye, and a control probe that hybridizes to a different region is labeled with a second dye. A nucleic acid that hybridizes to a stable portion of the chromosome of interest, such as the centromere region, is often most useful as the control probe. In this way, differences between efficiency of hybridization from sample to sample can be accounted for.

The FISH methods for detecting chromosomal abnormalities can be performed on nanogram quantities of the subject nucleic acids. Paraffin embedded tumor sections can be used, as can fresh or frozen material. Because FISH can be applied to the limited material, touch preparations prepared from uncultured primary tumors can also be used (see, e.g., Kallioniemi, A. et al., *Cytogenet. Cell Genet*. 60: 190–193 (1992)). For instance, small biopsy tissue samples from tumors can be used for touch preparations (see, e.g., Kallioniemi, A. et al., *Cytogenet. Cell Genet*. 60: 190–193 (1992)). Small numbers of cells obtained from aspiration biopsy or cells in bodily fluids (e.g., blood, urine, sputum and the like) can also be analyzed.

In various blot formats (e.g., dot blots, Southern blots, and Northern blots) nucleic acids (e.g., genomic DNA, cDNA or RNA) are hybridized to a probe specific for the target region. Either the probe or the target can be immobilized on the solid surface. Comparison of the intensity of the hybridization signal from the probe for the target region with the signal from a probe directed to a control (non amplified or deleted) such as centromeric DNA, provides an estimate of the relative copy number of the target nucleic acid. Procedures for carrying out Southern hybridizations are well known to those of skill in the art. see, e.g., Sambrook et al., supra.

Detection of Proteins of the Invention

The gene products described here, GLUT2 and PIK3CA, can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioiminunoassay(RIA), enzyme-linked immunosorbent assays (ELISAs), immunofluorescent assays, western blotting, and the like.

In a preferred embodiment, the proteins are detected using an immunoassay. As used herein, an immunoassay is an assay that utilizes an antibody to specifically bind to the analyte (e.g., GLUT2 or PIK3CA proteins). The immunoassay is thus characterized by detection of specific binding of the protein to an antibody raised against it as opposed to the use of other physical or chemical properties to isolate, target, and quantify the analyte (see, e.g., U.S. Pat. Nos. 4,366,241; 4,376,110; 4,517,288; and 4,837,168). For a review of the general immunoassays, see also *Methods in Cell Biology Volume 37: Antibodies in Cell Biology*, Asai, ed. Academic Press, Inc. New York (1993); *Basic and Clinical Immunology* 7th Edition, Stites & Terr, eds. (1991).

The proteins are preferably quantified in a biological sample derived from a mammal, more preferably from a human patient. As used herein, a biological sample is a sample of biological tissue or fluid that contains a protein concentration that may be correlated with amplification of the 3q regions disclosed here. Particularly preferred biological samples include, but are not limited to biological fluids such as blood or urine, or tissue samples including, but not limited to tissue biopsy (e.g., needle biopsy) samples.

The antibody (e.g., anti-GLUT2 or anti-PIK3CA) may be produced by any of a number of means well known to those of skill in the art (see, e.g. *Methods in Cell Biology Volume 37: Antibodies in Cell Biology*, Asai, ed. Academic Press, Inc. New York (1993); and *Basic and Clinical Immunology* 7th Edition, Stites & Terr, eds. (1991)). The antibody may be a whole antibody or an antibody fragment. It may be polyclonal or monoclonal, and it may be produced by challenging an organism (e.g. mouse, rat, rabbit, etc.) with one of these proteins or an epitope derived therefrom. Alternatively, the antibody may be produced de novo using recombinant DNA methodology. The antibody can also be selected from a phage display library screened against the protein (see, e.g. Vaughan et al. (1996) *Nature Biotechnology*, 14: 309–314 and references therein).

In other embodiments, Western blot (immunoblot) analysis is used to detect and/or quantify the presence of the proteins in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the desired protein. Other assay formats include liposome immunoassays (LIA), which use liposomes designed to bind specific molecules (e.g., antibodies) and release encapsulated reagents or markers. The released chemicals are then detected according to standard techniques (see, Monroe et al. (1986) *Amer. Clin. Prod. Rev.* 5:34–41).

The particular label or detectable group used in an immunoassay is not a critical aspect of the invention, so long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

Kits Containing Probes of the Invention

This invention also provides diagnostic kits for the detection of chromosomal abnormalities at the regions disclosed here. In a preferred embodiment, the kits include one or more probes to the regions described herein. The kits can additionally include blocking probes, instructional materials describing how to use the kit contents in detecting the alterations. The kits may also include one or more of the following: various labels or labeling agents to facilitate the detection of the probes, reagents for the hybridization including buffers, a metaphase spread, bovine serum albumin (BSA) and other blocking agents, sampling devices including fine needles, swabs, aspirators and the like, positive and negative hybridization controls and so forth.

EXAMPLES

Example 1

This example describes the identification of genes in a 2 MB region at 3q26.3 region. Increased copy number of this region is correlated with ovarian cancer.

CGH studies have identified DNA copy number abnormalities at 3q25–26 associated with ovarian tumors (Iwabuchi et al., *Cancer Research* 55:6172–8180 (1995)). To physically map the 3q26 region, a number of yeast artificial chromosome (YAC), P1, and cosmid clones that were known to genetically map to the region were physically mapped to the 3q region. Several yeast artificial chromosome (YAC) and P1 clones known to genetically map to this region were physically mapped using FISH and fractional length analysis. Clone positions were ee by PCR using STSs specific to the region. Clones were then picked according to their physical map position and hybridized onto interphase cells of ovarian cancer, breast cancer, and melanoma cell lines, as well as nuclei of paraffin-embedded ovarian tumors. One of the P1 clones and its 5 associated YAC clones have shown increases in copy number in 5 out of 5 ovarian cancer cell lines and 6 out of 6 primary ovarian tumor samples, small increases in copy number in the breast cancer lines, and no increases in copy number in the melanoma lines. Based on these results, the region of increased copy number was narrowed to a 2 MB region at 3q26.3.

Materials and Methods

Probes. Yeast artificial chromosome (YAC) clones were obtained from Genethon/CEPH of France. YAC clones were chosen based on their genetic map along 3q24-3qter. Each YAC was grown and checked for chimerism by FISH. P1 clones were obtained by screening a human genomic P1 library (DuPont, Boston, Mass.) using PCR with primers specific to chromosome 3. Those P1 clones mapping to 3q25-3qter were used for further study. A P1 clone mapping to the 3p region was used throughout the experiments as a reference marker.

Nonchimeric YAC clones as well as all the P1 clones were mapped onto chromosome 3 by digital image analysis of their physical distance from the terminus of the p arm (Flpter analysis) generally as described in Mascio, et al. *Cytometry* 19:51–9 (1995) and Sakamoto et al, *Cytometry* 19:60–9 (1995)).

All probes were labeled for hybridization by random priming (BioPrime kit, BRL). The 3q region probes were labeled with digoxigenin-11-dUTP (Boehringer-Mannheim) and detected using Fluorescein-antidigoxigenin. The reference P1 probe on 3p was directly labeled with Texas-Red dUTP (NEN DuPont).

Normal human metaphase spreads, cell lines, and paraffin-embedded tumor samples. Normal human metaphase spreads were prepared as previously described (Kallioniemi et al., supra). Slides were denatured in 70% formamide/2×SSC at 72 degrees for 3 to 10 minutes (depending on the slide batch) and then serially dried in 70%, 85%, and 100% ethanol.

Cell pellets of lines SKOV3, CAOV3, and OVCAR3 were obtained from ATCC. Cell pellets of lines G93, G95, 355, and 457 were kindly provided by Dr. Taetle (University of Arizona). All cells were resuspended in 2 ml of 0.075M KCl hypotonic solution, incubated at 37 degrees for 20 minutes, fixed, and dropped onto slides.

Paraffin-embedded epithelial ovarian tumor samples were provided by Dr. Teresa Yang-Feng (Yale University). All samples were checked to contain>60% tumor cells. These samples were deparaffinized, using xylene, washed with ethanol, then with water, digested with pepsin, and cytospun onto slides in order to concentrate the cell population.

FISH, physical mapping, and slide scorings. Cell line and normal metaphase slides were denatured in 70% formamide/2×SSC for 5 minutes at 72 degrees, followed by drying through 70%, 85%, and 100% ethanol. Paraffin-embedded tumor materials were fixed for 10 minutes in methanol-acetic acid (3:1) prior to denaturation in 70% formamide/2×SSC for 10 minutes at 80 degrees, then digested with 5 ug/Ml proteinase K for 10 minutes at 37 degrees, followed by drying through 70%, 85%, and 100% ethanol for 2 minutes each.

40 ng of each probe was placed on each slide along with 5 ug Cot1 DNA (to suppress repetitive sequences) in a total of 10 ul of 50% formamide/2×SSC/10% dextran sulfate, and slides were coverslipped and sealed. After an overnight incubation at 37 degrees, slides were washed to remove unbound probes, stained immunochemically with fluoresceinantidigoxigenin, counterstained with 0.2 uM 4,6-diamino-2-phenylindole in antifade solution for chromosome identification, and visualized under fluorescent microscope. For physical mapping, multicolor images of metaphase chromosomes and their associated probes were acquired using the QUIPS (quantitative image processing system). Analysis of the hybridization signals is completely automated, and carried out using the Xquips software (Mascio, et al. *Cytometry* 19:51–9 (1995) and Sakamoto et al, *Cytometry* 19:60–9 (1995)). Briefly, analysis consisted of chromosome segmentation, medial axis calculation, hybridization domain segmentation, center of mass calculation, and contrast enhancement. Fractional location of a domain was determined from the end of the short arm to the valid hybridization signal (Flpter analysis). On average, 20 Flpter measurements were made for each probe, and probe location on a chromosome was reported as the mean±one standard error of the mean of the measurements. Probe order was determined from the mean Flpter values.

For interphase cells, simultaneous Texas Red and Fluorescein signals were visualized using a double bandpass filter on the X63 objective of a Zeiss Axioscope camera. At least 100 cells were counted for each probe set.

Results

Figure 2A:
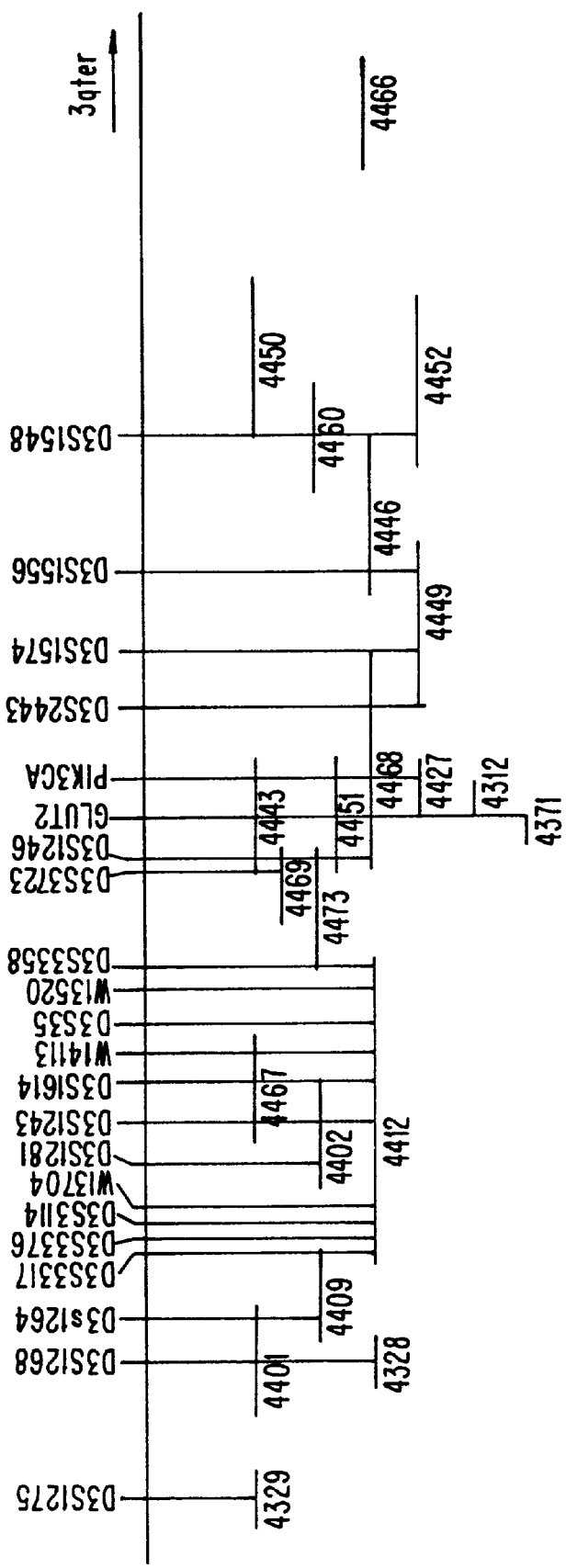
FIG. 2 shows clone order as used in this study. The vertical bars are the locations of the STS's overlapping the YAC and P1 clones, confirmed by PCR analysis. Clone order in these studies is confirmed further from Genethon and Whitehead data.
Figure 2B:
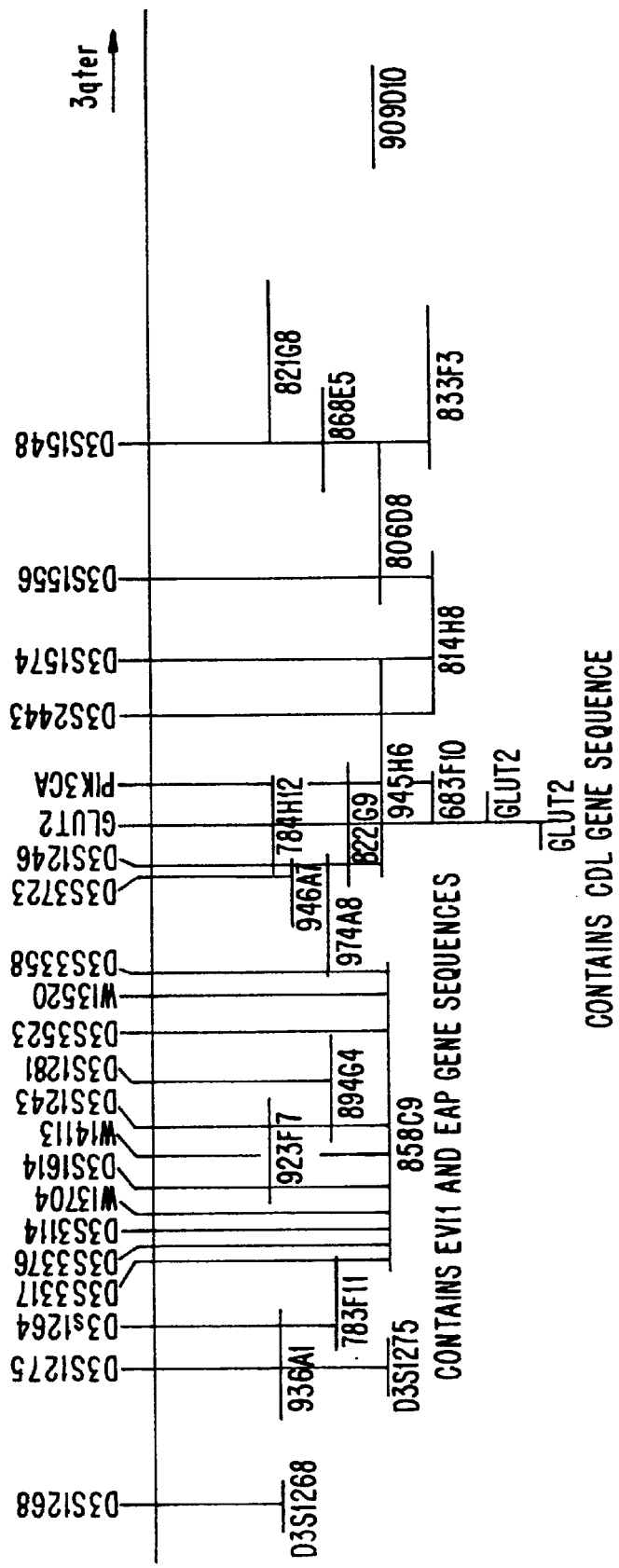
Figure 3A:
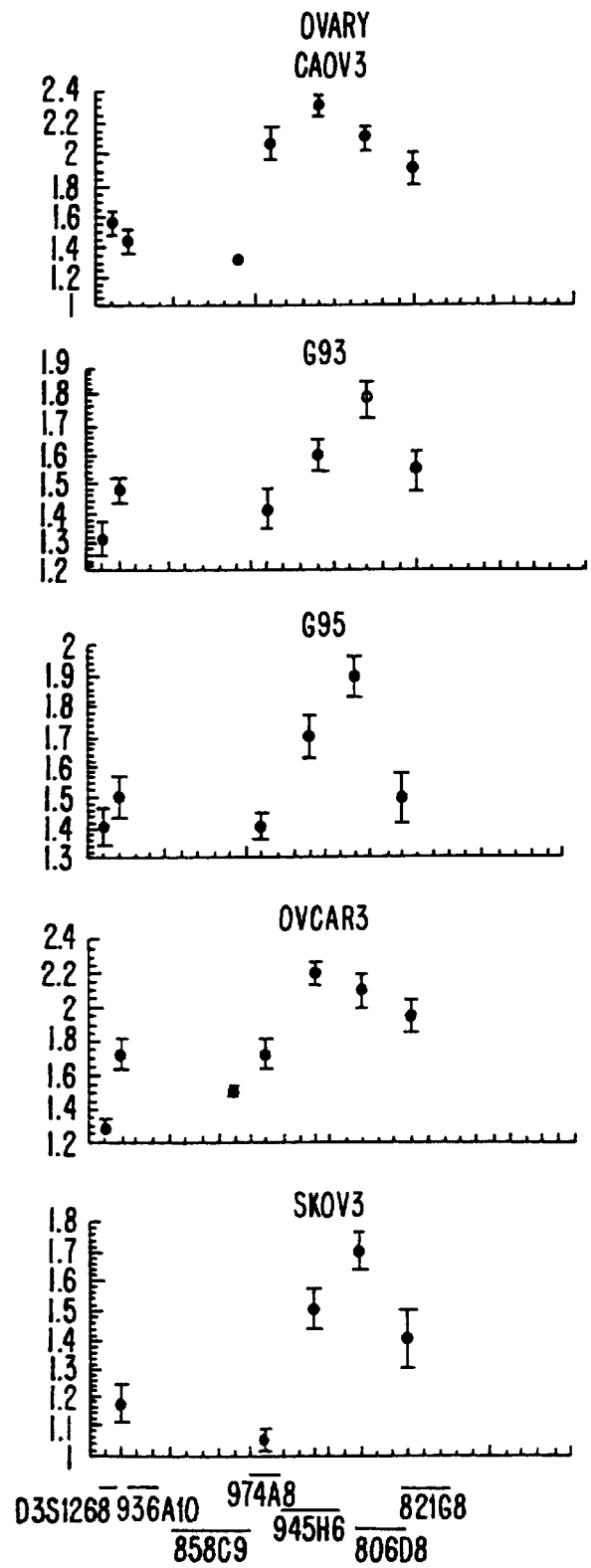
FIG. 3 shows ratios of green (test probe) to red (reference probe) signals as a function of probe position along the chromosome in ovarian cancer cell lines, breast cancer cell lines, and melanoma cell lines.
Figure 3B:
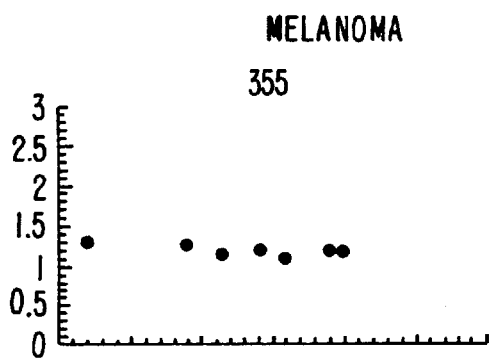
Figure 3B:
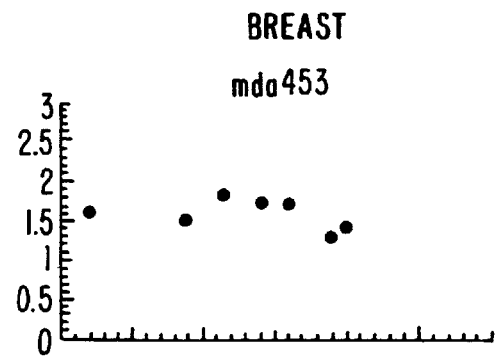
Figure 3B:
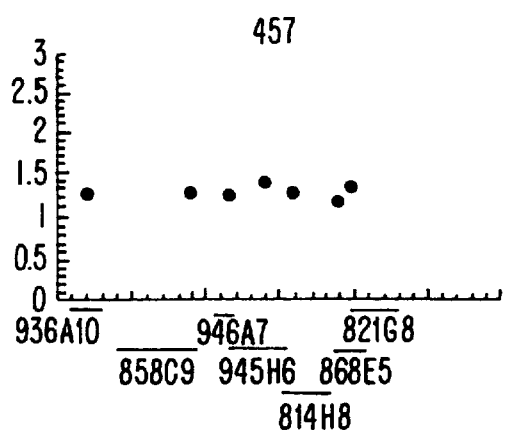
Figure 3B:
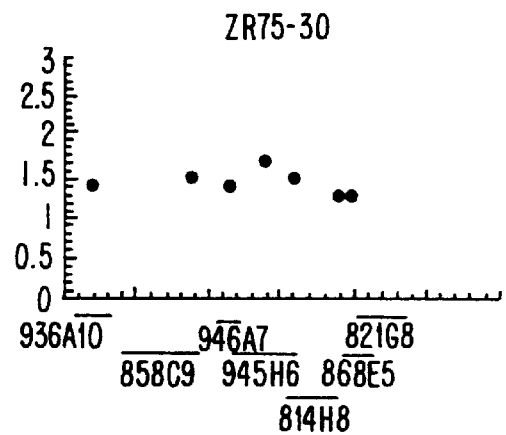

Physical mapping. FIG. 1 shows the order of all the P1s mapped along chromosome 3. In addition, the order of the clones for the region of interest was also checked by PCR using several STSs known to map to this region and confirmed by comparing these results to the recently published YAC maps in the Genome Directory Naylor et al., *Cytogenet. Cell Genet.* 72: 255–70 (1995) and the Whitehead institute's integrated map Dib et al., *Nature* 380:152–4 (1996). FIG. 2 shows the order of the clones as used in this study.

Copy number abnormalities in cancer cell lines for the 3q26 region. CGH studies delineated the region of increase in copy number at best to about 10 Megabases. FISH with well-mapped clones specific to the region was used to refine the region of increase in copy number on 3q26 in ovarian cancer to 2 megabases. FIG. 3 shows the data from hybridization experiments onto ovarian, breast, and melanoma cell lines. The graphs are relative copy numbers of the probes in the cell lines as a function of probe distance along the chromosome. One P1 clone, Glut2, and 5 YAC clones that share sequences with this P1 (683F10, 784H12, 806D8, 822G9, 945H6) consistently show increases in copy number in all ovarian cell lines. OVCAR3 shows a larger region of amplification throughout the region, with the aforementioned clones still manifesting the largest increase in copy number. Breast cancer lines ZR75-30 and mda453 showed a smaller increase in copy number for the same clones in the region, and melanoma lines 355 and 457 failed to show increases in copy number in this region.

Figure 4:
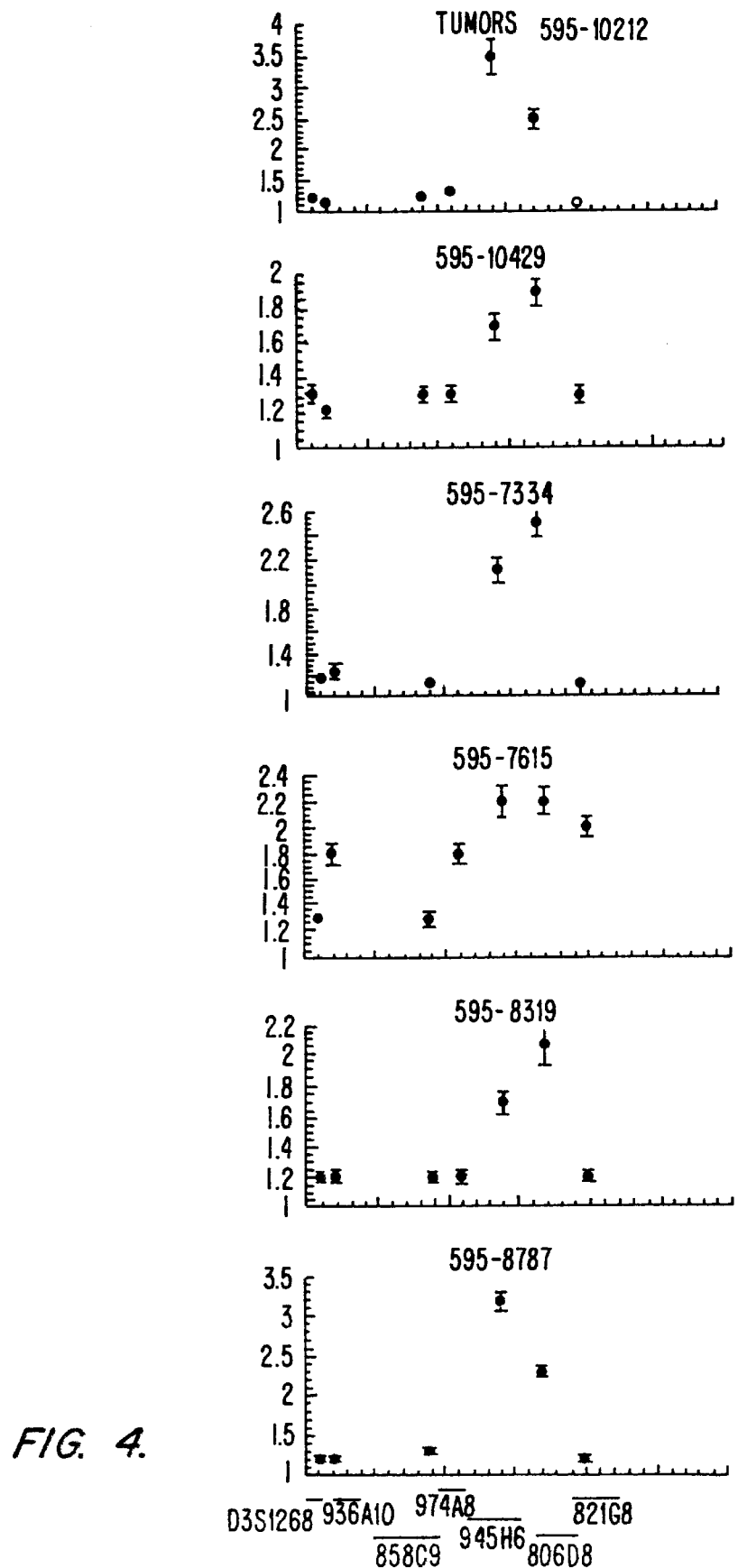
FIG. 4 shows relative copy number ratios in ovarian tumor samples.

Copy number abnormalities in ovarian tumor samples. All paraffin-embedded ovarian tumor samples also show the same regions of increase in copy umber that were seen in the ovarian cancer cell lines. As seen from FIG. 4, the region of increase in copy number is better defined in the tumor samples, with a sharp increase in the relative copy number for the P1 and its associated YACS. Increases in copy number for tumor sample 595-7615 seem to involve a larger amplicon, as all the probes tested in this tumor show a relatively elevated copy number.

Based on the FISH results of tumor samples and cell lines, we have delineated the critical region of increase in copy number in ovarian cancer on the long arm of chromosome 3 to the region of 3q26.3, spanning one P1 and 5 YACs that share sequences with this P1.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. A method of screening a sample for the presence of DNA copy number changes associated with cancer, the method comprising:

contacting a nucleic acid sample from a human patient with a first probe which binds selectively to a target nucleic acid sequence at 3q26.3, wherein the probe is contacted with the sample under conditions in which the probe binds selectively with the target nucleic acid sequence to form a stable hybridization complex;

contacting the sample with a second probe which binds selectively to a target nucleic acid sequence at 19q13.1–19q13.2, wherein the probe is contacted with the sample under conditions in which the probe binds selectively with the target nucleic acid sequence to form a stable hybridization complex; and detecting the formation of a first and a second hybridization complex, thereby detecting in the sample the presence of DNA copy number changes compared to normal, wherein the DNA copy number changes are associated with cancer.

2. The method of claim 1, wherein the target nucleic acid sequence to which the second probe binds is in an AKT2 gene.

* * * * *